United States Patent [19]
Ridgeway et al.

[11] Patent Number: 5,661,225
[45] Date of Patent: Aug. 26, 1997

[54] DYNAMIC DILUTION SYSTEM

[75] Inventors: Robert Gordon Ridgeway, Quakertown; Richard Vincent Pearce, Kempton; Peter James Maroulis, Mertztown; Seksan Dheandhanoo, Quakertown; Suhas Narayan Ketkar, Allentown, all of Pa.

[73] Assignee: Air Products and Chemicals, Inc., Allentown, Pa.

[21] Appl. No.: 712,765

[22] Filed: Sep. 12, 1996

[51] Int. Cl.$^6$ .................................................. G01N 33/00
[52] U.S. Cl. ...................................... 73/1.06; 137/7
[58] Field of Search ........................... 73/1 G, 31.03; 137/7, 3, 597, 599, 599.1, 897, 896, 605, 606, 861

[56] References Cited

U.S. PATENT DOCUMENTS

| | | | |
|---|---|---|---|
| 4,101,282 | 7/1978 | Ririe | 73/1 G |
| 4,290,296 | 9/1981 | Bredeweg et al. | 73/1 G |
| 5,054,309 | 10/1991 | Mettes et al. | 73/1 G |
| 5,214,952 | 6/1993 | Leggett et al. | 73/1 G |
| 5,239,856 | 8/1993 | Mettes et al. | 73/1 G |
| 5,587,519 | 12/1996 | Ronge et al. | 73/1 G |

*Primary Examiner*—Hezron E. Williams
*Assistant Examiner*—Nashmiya Ashraf
*Attorney, Agent, or Firm*—Geoffrey L. Chase

[57] ABSTRACT

An apparatus for generating a low concentration calibration gas mixture containing percent, ppm, ppb or ppt amounts of a desired analyte from a high concentration gas mixture and a high purity diluent using a series of source gas containing vessels and a series of parallel gas or chemical conduits controlled by mass flow controllers in a purged enclosure with conduits to purge gas conduits of residual gases or corrosive gases.

10 Claims, 2 Drawing Sheets

DYNAMIC DILUTION SYSTEM

TECHNICAL FIELD OF THE INVENTION

The present invention is a system for the dynamic dilution of a high concentration analyte containing gas to produce a low concentration analyte containing gas for calibrating analytical detectors, such as mass spectrometers and for analysis of emissions from process tools, combustion chambers and water based reactive gas removal systems.

BACKGROUND OF THE PRIOR ART

Industries, such as the electronics industry, have a need for analysis of industrial gases and other chemicals at very high purities with correspondingly low impurity levels. These levels have traditionally been at or below parts per million (ppm) by volume and are moving to parts per billion (ppb) by volume or parts per trillion (ppt) by volume for various impurity levels which can be tolerated in such gases or chemicals.

The electronics industry requires calibration gases for mass spectrometers, fourier transform infrared spectrometers and gas chromatographs. These calibration gases must have analytes in the ppm, ppb or ppt level by volume for the applications that they are utilized in for determining appropriate purity levels or emissions levels. The electronics industry also has the need for analysis of process tool emissions and subsequent containment devices, such as combustion chambers and water-based reactive gas removal systems.

The industry requires technology which allows for the generation of calibration gases having such low concentrations of analytes as standards where the standard is used at low pressure, in some instances below atmospheric pressure, the standard is a corrosive gas, or the standard is generated from a low volatility analyte source.

The industry has attempted to produce such standards such as is evidenced by U.S. Pat. No. 5,054,309 which dilutes a standard gas source with a raw gas in sequential series of steps to produce a low concentration gas mixture.

U.S. Pat. No. 5,214,952 describes a system for the production of ultra high purity calibration gas mixtures using mass flow controllers in a heated containment.

The prior art also includes systems such as depicted in FIG. 1 in which a diluent gas is mixed with a non corrosive gas or chemical in a permeation tube using mass flow controllers for the various process lines contained in an enclosure.

However, the prior art has not accomplished a dilution system for an array of gases or chemicals including non corrosive gases, low volatility gases or chemicals and corrosive gases in a manner providing for operator safety and low pressure delivery of low concentration calibration gas mixtures with necessary and appropriate purge functions for safety and purity assurance. These needs are solved by the present invention which will be set forth in greater detail below.

BRIEF SUMMARY OF THE INVENTION

The present invention is an apparatus for generating a low concentration calibration gas mixture for high purity gas analysis and chemical emissions monitoring equipment, comprising:

a) a first vessel to contain a high concentration non-corrosive gas with a first outlet conduit controlled by a first mass flow controller;

b) a second vessel to contain a high concentration corrosive gas with a second outlet conduit controlled by a second mass flow controller;

c) a third vessel to contain a low volatility high concentration chemical or gas with a third outlet conduit controlled by a third mass flow controller;

d) a source of high purity diluent gas;

e) a first diluent conduit to communicate the source of high purity diluent gas with each of the first, second and third outlet conduits through a mass flow controller to dilute the high concentration non-corrosive gas, the high concentration corrosive gas or such low volatility high concentration chemical or gas to produce the low concentration calibration gas mixture;

f) a second diluent conduit to communicate the source of high purity diluent gas with the first outlet conduit to purge the first outlet conduit through vent means in the first outlet conduit;

g) a third diluent conduit to communicate the source of high purity diluent gas with the second outlet conduit to purge the second outlet conduit through vent means in the second outlet conduit;

h) a fourth diluent conduit to communicate the source of high purity diluent gas with the third vessel to entrain the low volatility high concentration chemical or gas or to purge the third outlet conduit through vent means in the third outlet conduit;

i) means to control the pressure of the low concentration calibration gas;

j) a gas tight enclosure containing the first vessel, the first outlet conduit and the first mass flow controller, the second vessel, the second outlet conduit and the second mass flow controller, and the third vessel, the third outlet conduit and the third mass flow controller; and k) means to introduce purge gas into the enclosure and means to vent the purge gas from the enclosure.

Preferably, a permeation tube is connected to the third outlet conduit and a fifth diluent conduit to permeate low volatility high concentration chemical or gas into the diluent gas in the fifth diluent conduit.

Preferably, the means to control the pressure of the low concentration calibration gas mixture is a back pressure regulator and a variable rate leak valve.

Preferably, the second outlet conduit has means to heat the second outlet conduit and the third outlet conduit has means to heat the third outlet conduit.

Preferably, the first vessel, the second vessel and the third vessel are each industrial gas cylinders.

Preferably, the permeation tube is constructed of polytetrafluoroethylene.

Preferably, a high temperature mass flow meter is positioned in gas flow communication between the back pressure regulator and the leak valve to measure the flow of the low concentration calibration gas mixture.

Preferably, the permeation tube is in a temperature controlled containment.

Preferably, the gas tight enclosure has a gas flow sensor to sense the flow of purge gas and a warning signal which activates when the sensor indicates a flow less than a preset flow level.

Preferably, the conduits are high quality surface finish stainless steel tubing.

DETAILED DESCRIPTION OF THE INVENTION

Figure 1:
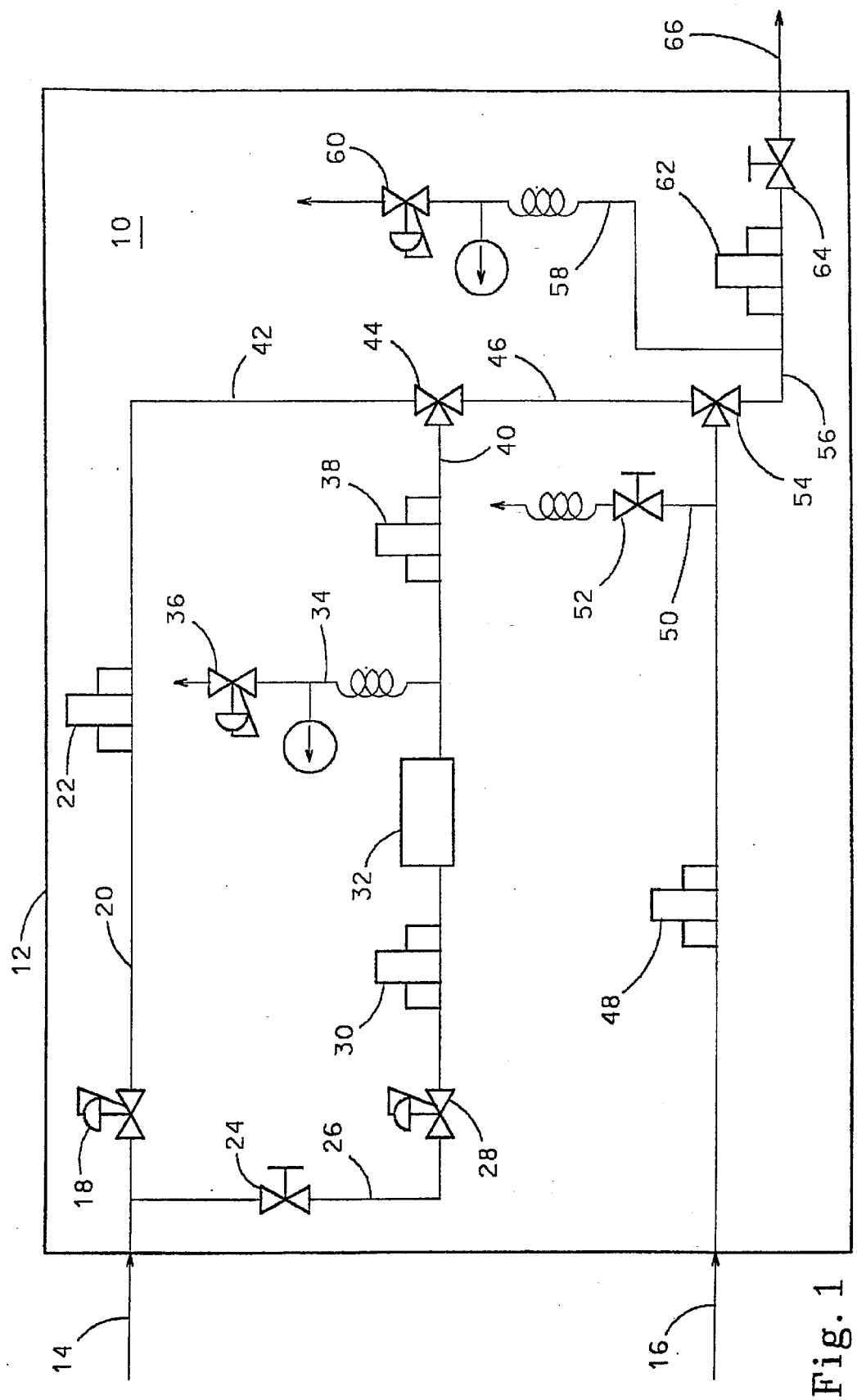
FIG. 1 is a schematic depiction of a prior art system to produce a calibration gas.

The Present Invention is an apparatus for dynamic dilution of high concentration gases or chemicals with a diluent, preferably an inert gas, to provide a low concentration calibration gas mixture for analytical equipment, particularly those used for the delivery of gas phase chemicals to the demanding requirements of the electronics industry.

Currently the electronics industry requires raw materials to be of high purity, typically less than percent levels of impurities by volume, preferably at least impurity levels no greater than single digit parts per million (ppm) by volume, and more preferably single digit parts per billion (ppb) by volume, and in some instances single digit parts per trillion (ppt) by volume.

The delivery of gases at such ultra high purities is subject to difficulties particularly with regard to the calibration of analytical equipment designed to measure or assure that the raw materials meet those high purity requirements. Most analytical equipment used to monitor such purities require recalibration periodically with various calibration standards. The calibration standards should be closely matched to the compositional makeup of the gas or chemicals being tested or monitored. The production of calibration standards at such low impurity or analyte levels such as parts per million (ppm) by volume, parts per billion (ppb) by volume, or parts per trillion (ppt) by volume, requires extreme care in the mixing or blending, as well as the storage or transport of such standards to the instrumentation being calibrated. Alterations in the desired impurity or analyte level or inadvertent doping of the standard can occur from various sources of contamination at such low impurity or analyte levels, such as surface reactions with materials of construction, off-gassing from various surfaces, adsorption and desorption phenomena in materials of construction, as well as inadvertent retention or pooling in various flow path geometries where flow allows for materials to accumulate.

The Present Invention is designed to produce such calibration standards in the form of a low concentration calibration gas mixture of the desired carrier gas or diluent and a doped quantity of the appropriate impurity or analyte for the purposes of calibrating analytical instruments, such as quadrupole mass spectrometers, fourier transform infrared spectrometers and gas chromatographs. Such equipment is used to certify the purity of gas phase chemicals delivered to meet the demanding requirements of the electronics industry, or to monitor fugitive emissions from semiconductor processing equipment and associated containment equipment. The low concentration of the desired analyte in the diluent is typically single digit percent by volume or less, preferably single digit ppm by volume, more preferably single digit ppb by volume and in some instances single digit ppt by volume.

A significant proportion of the sources of contamination or variation in the prepared calibration standards or low concentration calibration gas mixtures can be avoided by conducting the preparation of such low concentration calibration gas mixtures in a dynamic continuous flow mode. When the low concentration calibration gas mixtures are prepared in a dynamic continuous flow mode, contamination effects from adsorption/desorption and off-gassing can be at least rendered in a steady state condition if not eliminated, as well as eliminating the effects of flow path geometries where pooling or accumulation of gases might otherwise occur. Therefore, the apparatus of the Present Invention is designed for dynamic preparation of low concentration calibration gas mixtures and purging of appropriate flow pathways when continuous gas mixture preparation is not occurring. This is achieved by having a source of high purity diluent gas, which is typically an inert gas such as nitrogen, piped to various sources of high concentration chemical or gas from which the calibration standards are prepared.

In addition, the apparatus of the Present invention contemplates an enhanced degree of safety for the operators of the apparatus by providing the high concentration gas sources in a purged enclosure so as to avoid the dangers of any inadvertent leaking from process lines during utilization of the dynamic dilution apparatus of the Present Invention.

The apparatus of the Present Invention also provides discrete mixing flow paths for different classes of high concentration gas standards from which the low concentration calibration gas mixtures are prepared. For instance, a diluent gas, such as nitrogen, is separately piped to a source of non corrosive high concentration gas for metered mixture and dispensing to the instrumentation which requires calibration. This same diluent gas is also separately piped to an appropriate source of a high concentration corrosive gas which corrosive gas has special needs for handling to avoid degradation of the apparatus and initiation of contaminate inducing corrosion. In addition, some low concentration calibration gas mixtures are prepared from low volatility gases or liquid chemical precursors that are needed in gaseous form. The apparatus of the Present Invention provides a means for entraining these low volatility chemicals or gases in the diluent gas for transport to the instrument being calibrated. If necessary, the low volatility chemical or gas entrained in the diluent gas may be introduced into a permeation tube, which is typical in the industry, for the preparation of an exacting low concentration calibration gas mixture standard.

Each of the separate and discrete conduits used to mix diluent gas and high concentration chemical or gas is controlled by appropriate valving and mass flow controllers for controlled blending of the diluent and high concentration chemical or gas for appropriate production of precise and accurate low concentration calibration gas mixtures, typically containing no greater than single digit percent levels of doped contaminant or desired gas specie and more preferably single digit parts per million (ppm) levels of such doped contaminant. It is also possible to produce low concentration calibration gas mixtures having single digit parts per billion (ppb) levels of the desired doping material or contaminant and in some instances it is possible to have single digit parts per trillion (ppt) levels of these dopants or contaminants in the low concentration calibration gas mixture. All values are by volume.

To provide the necessary level of precision and consistency in the production of such low concentration calibration gas mixtures, the present apparatus is designed to provide dynamic mixing, where diluent gas and the appropriate high concentration chemical or gas are mixed continuously and immediately prior to utilization as a low concentration calibration gas mixture. Alternately, when preparation on a dynamic basis of the low concentration calibration gas mixture is not appropriate, the apparatus of the Present Invention provides for the continuous purging of the appropriate conduits with high purity diluent gas and the venting of such purged gas into separate exhaust conduits terminating via compression fittings at the wall of the gas tight enclosure. This purged gas flows to external exhaust lines and potential scrubbing under appropriate provisions typically available in electronic fabrication industry facilities.

The pressure of the low concentration calibration gas mixtures produced by the apparatus of the Present Invention is maintained by the cooperative utilization of a variable rate leak valve which is a valve designed for fine metered dispensing of material and the use of a pressure transducer and a back pressure regulator. This allows for only a metered quantity of low concentration calibration gas mixture to be dispensed to the analytical equipment being calibrated, while any additional low concentration calibration gas mixture produced can be vented from the system of the Present Invention when pressures exceed the set point of the back pressure regulator.

In the case of low volatility chemicals or gases, the apparatus of the Present Invention allows for entrainment in high purity diluent gas of such low volatility gas or chemical in a vapor phase to be contacted in a permeation tube, which is typically a polymeric polytetrafluoroethylene tube having a known permeation rate at determined gas flow rates and temperature of the surrounding environment of the permeation tube. These tubes are typically available in the industry, such as the Trace Source™ permeation tubes available from Kin-tek, 504 LaMarque, Texas 77568. The permeation tubes are used to dispense a very small, extremely stable flow of a component gas for making low concentration gas mixtures. The component gas contacts one side of a poly tetrafluoroethylene membrane. The vapor of the component gas slowly passes through the membrane by molecular permeation. The permeate is mixed with a controlled dilution flow of diluent gas to form the low concentration calibration gas mixture. The rate of permeation is determined by the temperature of the permeation tube and the flow of the low volatility gas or chemical entrained in the diluent and the flow of diluent gas.

The apparatus of the Present Invention provides enhanced safety by providing continuous purging, such as with house nitrogen, to the enclosure in which the apparatus is located. The purge gas and any gas leaking from the apparatus conduits is removed by a vent from the enclosure, which is typically piped to existing or stand alone vent and scrubber systems, as are well known in the art. The apparatus of the Present Invention provides for storage of reservoirs or vessels which contain the appropriate non corrosive high concentration gases, the corrosive high concentration gases and the low volatility high concentration gases or chemicals. In this manner, all of the sources of gaseous components, other than the inert diluent gas, are fully contained within the purged gas tight enclosure. Any venting for purposes of maintaining purity and cleanliness of process conduits vents to connections (compression fittings) located on the walls of the gas tight enclosure for subsequent external vent or scrubbing in existing systems or house facilities of known design. Any over pressure of the produced low concentration calibration gas mixture is also vented from the gas tight enclosure via fittings in the gas tight enclosure wall and removed for external venting or scrubbing through external piping to an exhaust system. These features allow for an enhanced degree of safety, as well as purity in the calibration gas producing apparatus of the Present Invention.

In the case of utilizing high concentration corrosive gas to prepare the low concentration calibration gas mixtures, the conduits through which the corrosive gas passes are heated to prevent retention of any of the gases on the inside surfaces of the conduit, where corrosion might occur to degrade the equipment and impair the high purity nature of the gas mixing apparatus.

Figure 2:
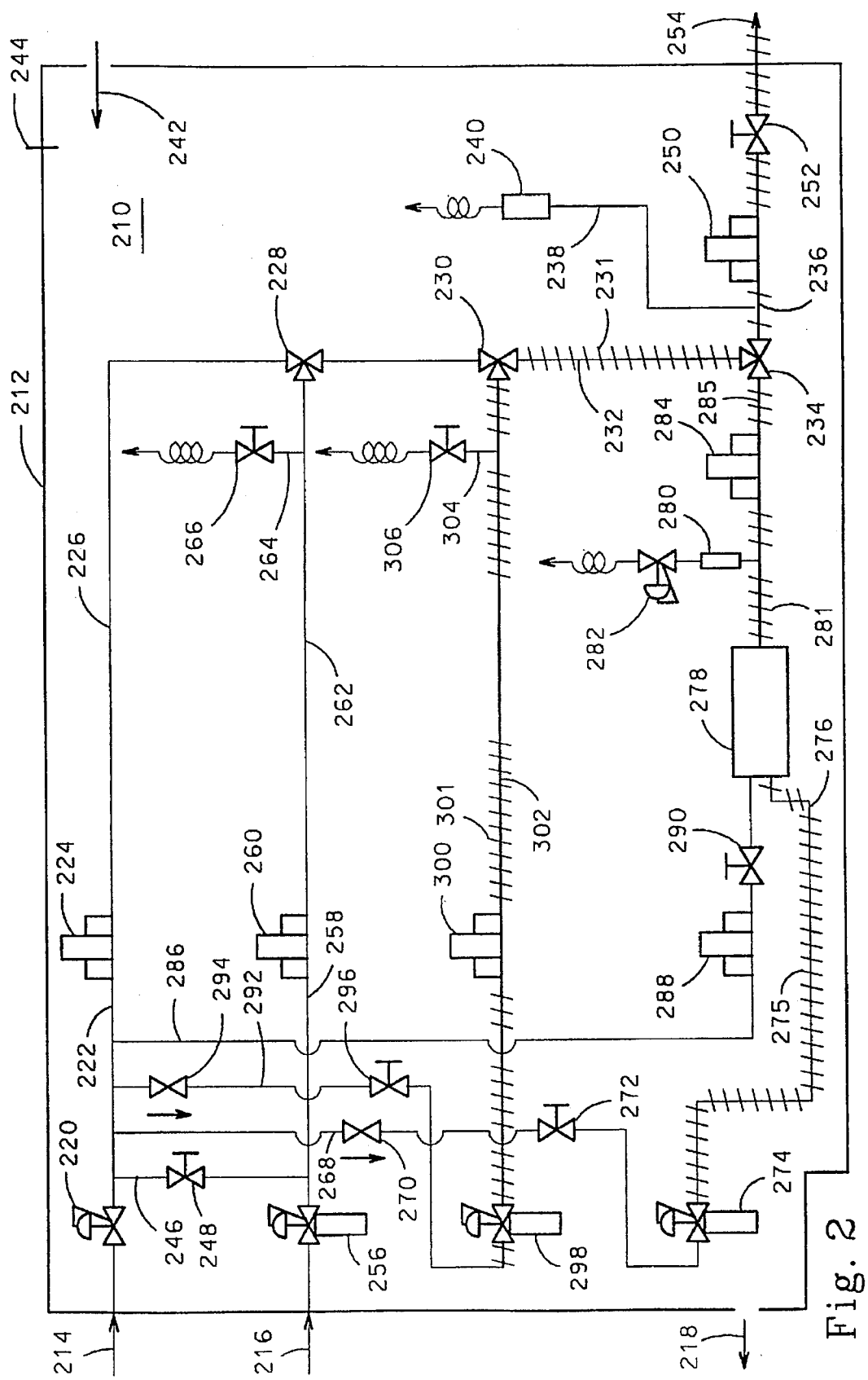
FIG. 2 is a schematic depiction of a preferred embodiment of the present invention.

Typical corrosive gases which may be utilized in the apparatus of the Present Invention include hydrogen fluoride, hydrogen chloride and chlorine. Typical non corrosive gases which may be used to prepare low concentration calibration gas mixtures in the apparatus of the Present Invention are hexafluoroethane and sulfur hexafluoride. These gas compositions comprise the analyte or specie to be analyzed for in the calibration gas standard being carried by the diluent or inert gas, such as nitrogen. Thus, the low concentration calibration gas mixture comprises a high purity diluent gas, such as nitrogen, doped with an appropriate, precise, low concentration (such as percent, parts per millions (ppm), parts per billion (ppb) or parts per trillion (ppt) by volume) of the analyte, such as hydrogen fluoride, hydrogen chloride, chlorine, hexafluoroethane or sulfur hexafluoride. Other gas species can easily be substituted for these identified gas species to be doped as an analyte into the inert gas. In addition to nitrogen, other inert gases can be contemplated, such as helium. It is also possible to produce a low concentration calibration gas mixture using an inert gas and water, which is introduced in a precise metered fashion through a permeation tube, as described above. This would provide for an accurate calibration of instruments seeking to determine water contamination in gas mixtures being supplied typically to an electronic fabrication facility. Liquid chemicals besides water can also be used in the permeation tube. Gas permeation is shown in FIG. 2.

The low concentration calibration gas mixtures are generated by blending known amounts of the diluent gas and the high concentration gas source. The amounts of the gas source and the diluent are controlled by high precision mass flow controllers. Based on the known concentration of analyte in the high concentration gas standards, the flow rates of the diluent and high concentration gas standard, the concentration of the analytes in the low concentration calibration gas mixture can be determined by the following equation:

$$C_x = (C_x^* S_p)/(S_p + S_d)$$

where $C_x^*$ and $C_x$ are the concentrations of analyte "x" in the high concentration gas source and the low concentration gas calibration gas mixture, respectively. $S_p$ is the flow rate of the high concentration gas source and $S_d$ is the flow rate of the diluent.

Due to the high level of analytes in the high concentration gas source, they can be easily quantified with high accuracy. The flow rates of the diluent and the high concentration gas source can be precisely measured. Therefore, the concentrations of analytes in the low concentration calibration gas mixture can be accurately determined, provided that there is no other source of analytes, such as off-gassing and adsorption/desorption effects. The off-gassing and the adsorption/desorption effects become negligible if the apparatus is clean and maintained in a dynamic flow condition. The present apparatus is maintained in such a dynamic flow condition by continuous purging and venting of lines not in direct operation.

Only a portion of the low concentration calibration gas mixture will be introduced into an analytical instrument for calibration. The remainder of the low concentration calibration gas mixture is vented from the apparatus through compression fittings in the wall of the gas tight enclosure for delivery to an external exhaust and scrubbing system. In order to obtain a steady flow rate of the low concentration calibration gas mixture, the pressure inside the low concentration calibration gas conduit is set and regulated by a back pressure regulator. The flow rate of the low concentration calibration gas mixture is measured by a mass flow meter prior to entering the analytic instrument to be calibrated. The flow rate and the pressure of the low concentration calibration gas mixture are controlled by a combination of the back pressure regulator and a variable rate leak valve, which is located between the mass flow meter and the analytical instrument being calibrated.

A system known in the prior art is depicted in FIG. 1. The apparatus 10 has enclosure 12 and the source of the diluent gas 14 and a non corrosive calibration gas 16. When mixing the diluent gas with a non corrosive calibration gas, the diluent is controlled through valve 18 and line 20 to pass through a mass flow controller 22 and in line 42 to pass through three way valve 44 and line 46. The non corrosive calibration gas is metered through mass flow controller 48 and either through vent line 50 controlled by valve 52 or introduced into three way valve 54 to be blended with the diluent as a combined calibration gas in line 56, capable of being vented in line 58 controlled by back pressure regulator 60. The calibration gas is measured through mass flow meter 62 and leak valve 64 to be sent to down stream calibration utilization in line 66.

Alternatively, the diluent can pass through valve 24 in line 26 for control in pressure regulator 28 and mass flow controller 30 before passing through a temperature control permeation tube 32 where moisture can be entrained in the diluent gas for producing a moisture calibration standard. This gas can be vented in line 34 through back pressure regulator 36 or utilized in incremental controlled amounts by passing through mass flow controller 38 in line 40 to be mixed with additional diluent through three way valve 44 using the diluent in line 42.

The drawbacks of this prior art system are the lack of containment for source gases, particularly if they are corrosive, the lack of purge gas and any warning signals for dangerous circumstances, the lack of means to entrain low volatility gases or chemicals and the lack of heating or heat tracing in the event a corrosive gas would be used to develop a calibration standard.

The Present Invention, which improves upon the prior art techniques for producing calibration standards, will now be described in greater detail with reference to a preferred embodiment illustrated in FIG. 2. The apparatus for dynamic dilution 210 includes a gas tight enclosure 212 with orifices for introducing a inert high purity diluent 5 gas 214, such as nitrogen, and another orifice for introducing non corrosive high concentration gas in line 216, as well as a purge gas inlet 242 and a purge outlet 218 which is monitored by an appropriate sensor or warning signal or light 244. The sensor 244 can be connected with appropriate controls to shut off all gas flows if a default condition is detected. The ultimate low concentration calibration gas mixture containing the appropriately chosen analyte is dispensed through conduit 254.

Diluent is controlled through pressure regulator 220 and is introduced via first diluent conduit 222 into mass flow controller 224 for metered, accurate, calibrated dispensing in conduit 226 for mixture with one of several high concentration gas sources of either non corrosive gas, corrosive gas or a low volatility gas or chemical. A high concentration non corrosive gas provided in conduit 216 or a first vessel 256 is dispensed in first outlet conduit 258 under the control of first mass flow controller 260 which provides precise calibrated metering of the flow of the gas. This gas in conduit 262 may be vented in vent conduit 264 controlled by valve 266 or mixed with the diluent in conduit 226 through three way valve 228. The resulting low concentration calibration gas mixture passes through valve 230 which is closed with respect to conduit 302 and further passes through valve 234 again closed with respect to conduit 285 and passes out through conduit 236 under the control of high temperature mass flow meter 250 and variable rate leak valve 252 which controls the pressure of the low concentration calibration gas mixture even to the point of being sub-atmospheric for appropriate utilization downstream through conduit 254.

Alternatively, when high concentration non corrosive gas in conduit 216 or first vessel 256 is not being utilized, diluent gas passes through second diluent conduit 246 and valve 248 to conduit 258 and 262 for venting through conduit 264 and valve 266 to an appropriate compression fitting in the sidewall of the gas tight enclosure 212 and connected to an external vent system and potentially scrubber system not shown, but typical of those in use in the electronics industry's fabrication facilities.

Diluent gas in conduit 214 may also be blended with high concentration corrosive gas in a second vessel 298 which is dispensed through second outlet conduit 302 under the control of a second high temperature mass flow controller 300 and as illustrated under heated conditions with heat tracing 301. The high concentration gas blends with the diluent in three way valve 230 and passes through conduit 232 which is also heated by heat tracing 231. The resulting low concentration corrosive calibration gas mixture passes through three way valve 234 while conduit 285 is closed and travels through heated conduit 236 and high temperature mass flow controller 250 to be dispensed through variable rate leak valve 252 for ultimate utilization in conduit 254. The heat tracing on all of the lines through which the corrosive gas passes, in either its high concentration state or its low concentration calibration gas mixture state, precludes detrimental effects from the corrosive gas occurring on the inner surfaces of the gas flow streams or conduits and control equipment by keeping the gas vaporized and uncondensed on those surfaces, which are typically high quality surface finish stainless steel.

When the apparatus 210 is not being utilized to produce a low concentration corrosive calibration gas mixture, the diluent gas in conduit 222 may be passed through check valve 294 and third diluent conduit 292 and further valve 296 to purge the valve fittings of second vessel 298 and conduit 302 with venting through conduit 304 and valve 306 through an appropriate compression fitting to vent the gas in an exhaust line external to the gas tight enclosure 212 via existing vent systems outside the enclosure 212, including existing scrubber systems, typical of the electronics industry. This precludes detrimental effects of the corrosive gas on the inner surfaces of the gas flow paths and minimizes any subsequent contamination either by stagnant corrosive gas or corrosion, which could occur while the corrosive gas remained in that part of the flow path.

Diluent gas may also be mixed with a low volatility gas or chemical in a third vessel 274, whereby diluent in fourth diluent conduit 268 controlled by valve 270 and 272 passes through the third vessel 274 to volatilize the low volatility high concentration gas into third outlet conduit 276. Diluent in fifth diluent conduit 286 is then metered through mass flow controller 288 and valve 290 to pickup the low volatility gas or chemical in permeation tube 278, whereby the diluent gas passing through valve 290 is on one side of a polytetrafluoroethylene permeation membrane of the permeation tube from the low volatility gas or chemical in conduit 276. The resulting low concentration calibration gas mixture comprising the low volatility gas or chemical in the diluent gas passes through a high temperature third mass flow controller 284 and conduit 285 and exits through valve 234, conduit 236 and high temperature mass flow meter 250, whereby its pressure is controlled by variable rate leak valve 252 with ultimate dispensing for downstream calibration standard utilization in conduit 254. In the event that the low volatility high concentration gas in third vessel 274 is corrosive, conduits 276 and 285 are also heat traced 275, 281, respectively, to preclude condensation and corrosion problems. When this series of conduits servicing the third vessel 274 is off line, diluent gas in conduit 222 may be utilized to purge conduit 268 or 286 with venting through pressure transducer 280 and back pressure regulator 282 through a compression fitting in the side wall of gas tight enclosure 212 for delivery to an external exhaust system typical of the electronics industry and/or scrubber system, not shown. Preferably, the permeation tube 278 is maintained in a temperature controlled containment, not shown, to enhance the accuracy of the permeation rate.

The apparatus of the Present Invention has been described with reference to a particular preferred embodiment. It is conceivable to have variations from this particular embodiment. However, the advantages that flow from the apparatus of the Present Invention are the safety for operator utilization and the ability to produce calibration standards or low concentration calibration gas mixtures from an array of different analyte sources or high concentration gases, including: non-corrosive calibration source gases, corrosive calibration gas sources and low volatility gases or chemicals, which may either be corrosive or non corrosive.

In addition, the apparatus of the Present Invention with the utilization of a leak valve and a pressure transducer in the downstream or dispensing portion of the apparatus allows for accurate pressure control of the low concentration calibration gas mixtures even for dispensing of calibration gas standards which are below ambient or atmospheric pressure. Any over pressurization in the dynamic dilution or mixing of the diluent and the calibration source gas can be vented through conduit 238 and pressure transducer/back pressure regulator 240 out of the gas tight enclosure 212 through connection with appropriate exhaust line and scrubbing systems outside of the enclosure 212.

The apparatus of the Present Invention also provides appropriate flow paths so that diluent gas may be utilized to continue to make low concentration calibration gas mixtures with other gas sources while an offstream gas source and its appropriate conduits and lines may be continually purged to prevent buildups of contaminants and avoidance of corrosion simultaneous with the operation of gas mixture production.

The apparatus of the Present Invention is designed and dimensioned so as to permit containment of the high concentration calibration gas sources within the purged enclosure for safety of operators. The first, second and third vessels 256, 298 and 274 can comprise industrial gas cylinders typically of the size known as a lecture bottles, which typically have a capacity of 0.43 liters.

A benefit of the Present Invention, wherein discrete flow paths for the various calibration gas standards are utilized, is that appropriate design for corrosive gases can be individually provided in the conduits downstream of the vessel containing the corrosive calibration gas source. This includes specific geometries to avoid buildup of corrosive gas at surfaces or seals which might be sensitive to corrosive gas contact, as well as appropriate heating by heat trace or heat tape to avoid condensation and collection of corrosive gas on parts that would otherwise be subject to some actions of the corrosive gas producing particulates and degradation of the equipment.

The apparatus of the Present Invention further allows for utilization of low volatility calibration gas sources or chemicals to be made into low concentration calibration gas mixtures via the appropriate piping for entrainment of such low volatility gases and chemicals and controlled permeation through an appropriate permeation tube. These flow paths for the low volatility gas or chemical may also be purged, which is appropriate for a low volatility gas or chemical, particularly if it has corrosive nature because this would provide a far more aggravating gas specie in the process flow conduits than for higher volatility gases and chemicals.

As a result, the apparatus of the Present Invention provides a safe, contained means for producing calibration gas standards from an array of differing classes of calibration gas sources in a dynamic manner wherein the flow paths and conduits of the apparatus may be maintained under continuous flow conditions either of gases to be mixed or inert diluent gases which perform a purge function.

This apparatus results in production of low concentration calibration gas mixtures where the spiked or doped chemical specie or analyte can be present in high precision low concentration levels typically at or less than single digit percents by volume and more typically in single digit parts per million (ppm) by volume, preferably single digit parts per billion (ppb) by volume and in some instances single digit parts per trillion (ppt) by volume.

These capabilities represent a unique solution to an outstanding problem posed by the needs of the electronic industry as it designs computer chips having dimensions in the submicron level. The apparatus of the Present Invention, unlike systems in the prior art, provides a latitude of capability to produce low concentration calibration gas mixtures from a wide array of gas species under dynamic conditions and continually clean gas mixing parameters for high quality calibration of analytical instrumentation typically used in the electronics and the industrial gas industry, such as spectrometers and gas chromatographs. For the analysis of high purity gases, concentrations at or below ppm levels are needed as calibration standards. For effluent analysis, concentrations from ppm to percent levels for calibration standards are typically required.

The Present Invention has been described with regard to a particular preferred embodiment, however, the scope of the Present Invention should be ascertained from the claims which follow.

We claim:

1. An apparatus for generating a low concentration calibration gas mixture for high purity gas analysis and chemical emissions monitoring equipment, comprising:
   a) a first vessel to contain a high concentration non-corrosive gas with a first outlet conduit controlled by a first mass flow controller;
   b) a second vessel to contain a high concentration corrosive gas with a second outlet conduit controlled by a second mass flow controller;
   c) a third vessel to contain a low volatility high concentration chemical or gas with a third outlet conduit controlled by a third mass flow controller;
   d) a source of high purity diluent gas;
   e) a first diluent conduit to communicate the source of high purity diluent gas with each of said first, second and third outlet conduits through a mass flow controller to dilute said high concentration non-corrosive gas, said high concentration corrosive gas or such low volatility high concentration chemical or gas to produce said low concentration calibration gas mixture;

f) a second diluent conduit to communicate said source of high purity diluent gas with said first outlet conduit to purge said first outlet conduit through vent means in said first outlet conduit;

g) a third diluent conduit to communicate said source of high purity diluent gas with said second outlet conduit to purge said second outlet conduit through vent means in said second outlet conduit;

h) a fourth diluent conduit to communicate said source of high purity diluent gas with said third vessel to entrain said low volatility high concentration gas or to purge said third outlet conduit through vent means in said third outlet conduit;

i) means to control the pressure of said low concentration calibration gas;

j) a gas tight enclosure containing said first vessel, said first outlet conduit and said first mass flow controller, said second vessel, said second outlet conduit and said second mass flow controller, and said third vessel, said third outlet conduit and said third mass flow controller; and k) means to introduce purge gas into said enclosure and means to vent said purge gas from said enclosure.

2. The apparatus of claim 1 wherein a permeation tube is connected to said third outlet conduit and a fifth diluent conduit to permeate low volatility high concentration gas into the diluent gas in said fifth diluent conduit.

3. The apparatus of claim 1 wherein said means to control the pressure of said low concentration calibration gas mixture is a back pressure regulator and a variable rate leak valve.

4. The apparatus of claim 1 wherein said second outlet conduit has means to heat said second outlet conduit and said third outlet conduit has means to heat said third outlet conduit.

5. The apparatus of claim 1 wherein said first vessel, said second vessel and said third vessel are each industrial gas cylinders.

6. The apparatus of claim 2 wherein said permeation tube is constructed of polytetrafluoroethylene.

7. The apparatus of claim 3 wherein a high temperature mass flow meter is positioned in gas flow communication between said back pressure regulator and said leak valve to measure the flow of said low concentration calibration gas mixture.

8. The apparatus of claim 2 wherein said permeation tube is in a temperature controlled containment.

9. The apparatus of claim 1 wherein said gas tight enclosure has a gas flow sensor to sense the flow of purge gas and a warning signal which activates when said sensor indicates a flow less than a preset flow level.

10. The apparatus of claim 1 wherein said conduits are high quality surface finish stainless steel tubing.

* * * * *